United States Patent [19]

Datta et al.

[11] Patent Number: 5,607,415
[45] Date of Patent: Mar. 4, 1997

[54] FLEXIBLE ABSORBENT ARTICLE

[75] Inventors: Paul J. Datta, Appleton; Joseph D. Coenen, Menasha; Glenn A. Mintern, Appleton; David W. Powell, Neenah, all of Wis.

[73] Assignee: Kimberly-Clark Corporation, Neenah, Wis.

[21] Appl. No.: 292,561

[22] Filed: Aug. 18, 1994

[51] Int. Cl.$^6$ .............................. A61F 13/15; A61F 13/20
[52] U.S. Cl. ..................... 604/385.1; 604/370; 604/380; 604/386
[58] Field of Search .................... 604/369, 374, 604/377–378, 379, 380, 385.1, 366, 370, 386

[56] References Cited

U.S. PATENT DOCUMENTS

| | | | |
|---|---|---|---|
| 3,236,238 | 2/1966 | Morse | 604/370 |
| 3,687,350 | 8/1972 | Warburton | 229/2.5 |
| 3,776,233 | 12/1973 | Schaar | 604/385.1 |
| 3,805,790 | 4/1974 | Kaczmarzyk et al. | 128/290 R |
| 3,954,107 | 5/1976 | Chesky et al. | 604/374 |
| 4,059,114 | 11/1977 | Richards | 128/287 |
| 4,554,191 | 11/1985 | Korpman | 428/35 |
| 4,677,810 | 7/1987 | Spano | 53/428 |
| 4,681,577 | 7/1987 | Stern et al. | 604/378 |
| 4,685,914 | 8/1987 | Holtman | 604/368 |
| 4,699,823 | 10/1987 | Kellenberger et al. | 428/219 |
| 4,728,381 | 3/1988 | Jezuit et al. | 156/245 |
| 4,730,761 | 3/1988 | Spano | 225/2 |
| 4,740,342 | 4/1988 | Menard et al. | 264/549 |
| 4,752,349 | 6/1988 | Gebel | 156/267 |
| 4,778,372 | 10/1988 | Mutti et al. | 425/294 |
| 4,781,710 | 11/1988 | Megison et al. | 604/378 |
| 4,798,603 | 1/1989 | Meyer et al. | 604/378 |
| 4,798,638 | 1/1989 | Marbach | 156/69 |
| 4,814,123 | 3/1989 | Hautemont | 264/40.6 |
| 4,820,295 | 4/1989 | Chapas et al. | 604/385.1 |
| 4,822,332 | 4/1989 | Kajander | 604/16 |
| 4,828,555 | 5/1989 | Hermansson | 606/379 |
| 4,865,597 | 9/1989 | Mason, Jr. et al. | 604/385.1 |
| 4,886,513 | 12/1989 | Mason, Jr. et al. | 604/385.1 |
| 4,897,084 | 1/1990 | Ternstrom et al. | 604/385.2 |
| 4,936,839 | 6/1990 | Molee et al. | 604/378 |
| 4,944,735 | 7/1990 | Mokry | 604/366 |
| 4,950,262 | 8/1990 | Takagi | 604/385.1 |
| 5,013,309 | 5/1991 | Baigas, Jr. et al. | 604/368 |
| 5,030,229 | 7/1991 | Yang | 604/385.1 |
| 5,074,856 | 12/1991 | Coe et al. | 604/385.1 |
| 5,098,422 | 3/1992 | Davis et al. | 604/385.1 |
| 5,129,893 | 7/1992 | Thoren | 604/385.2 |
| 5,147,343 | 9/1992 | Kellenberger | 604/368 |
| 5,171,302 | 12/1992 | Buell | 604/385.1 |
| 5,178,139 | 1/1993 | Angelillo et al. | 128/403 |
| 5,181,563 | 1/1993 | Amaral | 604/385.2 |

FOREIGN PATENT DOCUMENTS

| | | |
|---|---|---|
| 0136524 | 4/1985 | European Pat. Off. . |
| 0256871A2 | 2/1988 | European Pat. Off. . |
| 0321980 | 6/1989 | European Pat. Off. . |
| 0335253 | 10/1989 | European Pat. Off. . |
| 0483592 | 5/1992 | European Pat. Off. .............. 604/377 |
| 0605017 | 7/1994 | European Pat. Off. . |
| 9210984 | 7/1992 | WIPO . |
| 9301785 | 2/1993 | WIPO ................. 604/385.1 |
| 96/13237 | 5/1996 | WIPO . |

*Primary Examiner*—John G. Weiss
*Assistant Examiner*—Bruce Snow
*Attorney, Agent, or Firm*—Thomas M. Gage

[57] ABSTRACT

An absorbent article includes a moisture barrier formed of a formable, liquid impermeable material. The moisture barrier defines a basin having a width dimension, a length dimension greater than the width dimension, and a volume. The basin includes a floor having corrugations formed therein parallel to the width dimension. The absorbent article also includes an absorbent assembly disposed within the basin and a liner formed of a liquid permeable material bonded to the moisture barrier and sandwiching the absorbent assembly therebetween. The corrugations permit the absorbent article to bend inwardly, for example to conform to the shape of the wearer, without bunching the moisture barrier along the portions facing the wearer and without substantially stretching or deforming the floor of the moisture barrier.

17 Claims, 4 Drawing Sheets

FLEXIBLE ABSORBENT ARTICLE

BACKGROUND OF THE INVENTION

The present invention is directed to a flexible absorbent article for containing and absorbing bodily discharges. More particularly, the invention pertains to a disposable absorbent article having a formed moisture barrier that is adapted to fit comfortably against the body of the wearer.

Disposable absorbent articles contain and absorb urine and other body exudates, and have been designed for people of all ages. Most absorbent articles have several common components, such as a liquid pervious bodyside liner, a liquid impervious moisture barrier, an absorbent material disposed between the bodyside liner and the moisture barrier, and some form of attachment system for securing the product about the body of the wearer.

In some instances, particularly adult incontinence products, the moisture barrier consists of a formable material that retains a three-dimensional shape. The formable material can be set in the three-dimensional shape by manufacturing processes such as thermoforming, vacuum forming, injection molding or mechanical forming. Formable materials processed by these techniques provide a certain degree of rigidity, which beneficially functions to maintain the shape of the moisture barrier during use and allow the absorbent article to fill to its capacity.

One drawback of formed moisture barriers, however, stems from this ability to retain a three-dimensional shape. Formed, three-dimensional moisture barriers do not readily conform to the shape of the wearer, a factor which can impact comfort and absorbency. To improve the body conformity of formed moisture barriers, manufacturers have produced such materials with a predetermined longitudinally curved shape. While this addresses the needs of some consumers, it does not entirely remedy the problem due to the variety of shapes of wearers. Further, formed products with a predetermined curved shaped present particularly challenging manufacturing hurdles.

Therefore, what is lacking and needed in the art is an improved absorbent article with a formed moisture barrier that is adapted to conform to the shape of the wearer.

SUMMARY OF THE INVENTION

In response to the discussed deficiencies in the prior art, a new disposable absorbent article has been developed. The absorbent article employs a formed moisture barrier that generally retains its shape during use and is also easily bendable so that the article can conform to the shape of the wearer.

In one aspect, the invention pertains to an absorbent article including a moisture barrier formed of a formable, liquid impermeable material. The moisture barrier defines a basin having a width dimension, a length dimension greater than the width dimension, and a volume. The basin includes a floor having corrugations formed in the floor parallel to the width dimension. An absorbent assembly of the absorbent article is disposed within the basin, and a liner formed of a liquid permeable material is bonded to the moisture barrier to sandwich the absorbent assembly therebetween.

In another aspect, the invention pertains to an absorbent article adapted for attachment to clothing. The absorbent article includes a moisture barrier formed of a formable, liquid impermeable material and defining a basin having a width dimension, a length dimension greater than the width dimension, and a volume. The basin includes a floor and a peripheral wall surrounding the floor, where the floor has first and second longitudinally spaced end regions and an extendable region between the end regions. The extendable region includes from about 2 to about 100 corrugations formed therein parallel to the width dimension. The absorbent article also includes means for attaching the moisture barrier to clothing, which means include an adhesive disposed on the floor solely in the end regions. An absorbent assembly of the absorbent article is disposed within the basin, and a liner formed of a liquid permeable material is bonded to the moisture barrier to sandwich the absorbent assembly therebetween.

In still another aspect, the invention pertains to an absorbent article with a moisture barrier formed of a formable, liquid impermeable material. The moisture barrier defines a basin having a width dimension, a length dimension greater than the width dimension, and a volume. The basin includes a floor having first and second longitudinally spaced end regions and an extendable region between the end regions, where the extendable region includes corrugations formed in the floor parallel to the width dimension. The floor includes rib means which extend parallel to the width dimension for providing enhanced resistance to transverse compression of the moisture barrier. The absorbent article also includes an absorbent assembly disposed within the basin, and a liner formed of a liquid permeable material bonded to the moisture barrier to sandwich the absorbent assembly therebetween.

Yet another aspect of the invention relates to a method of making an absorbent article. The method includes the steps of: providing a formable sheet of liquid impermeable material; providing an absorbent assembly; providing a sheet of liquid permeable material; providing a mold surface; forming the formable sheet on the mold surface to produce a moisture barrier defining a basin having a width dimension, a length dimension greater than the width dimension, and a volume, the basin comprising a floor having corrugations formed in the floor parallel to the width dimension; disposing the absorbent assembly in the basin; and bonding the sheet of liquid permeable material to the moisture barrier to sandwich the absorbent assembly therebetween.

Numerous features and advantages of the present invention will appear from the following description. In the description, reference is made to the accompanying drawings which illustrate preferred embodiments of the invention. Such embodiments do not represent the full scope of the invention. Reference should therefore be made to the claims herein for interpreting the full scope of the invention.

DEFINITIONS

Figure 1:
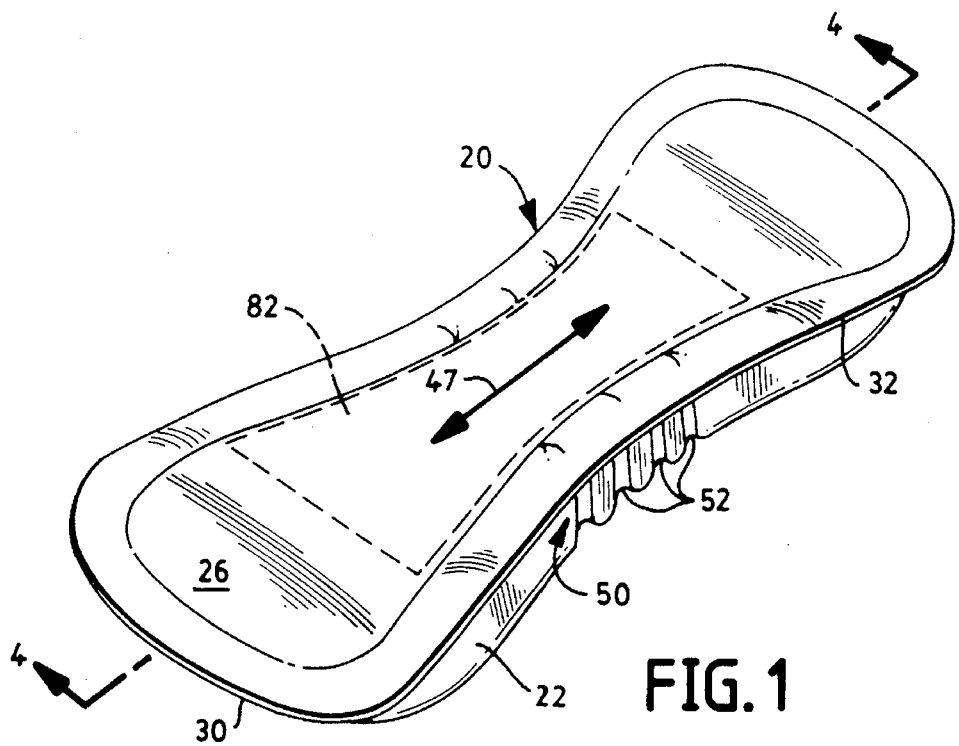
FIG. 1 is a perspective view of a disposable absorbent article according to the present invention.
Figure 2:
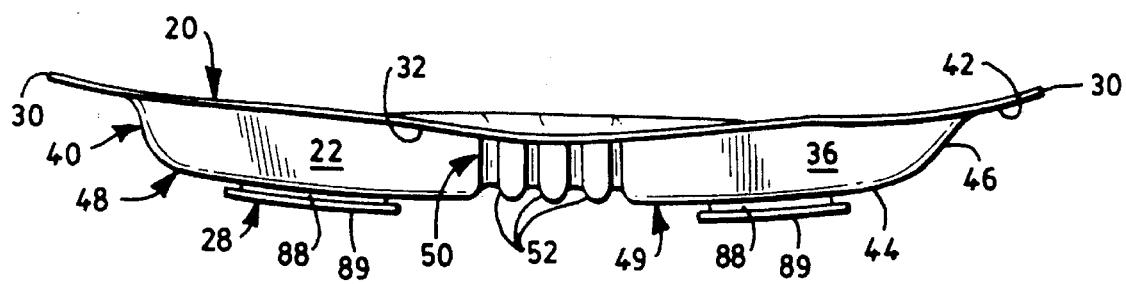
FIG. 2 is a side view of the disposable absorbent article shown in FIG. 1.
Figure 3:
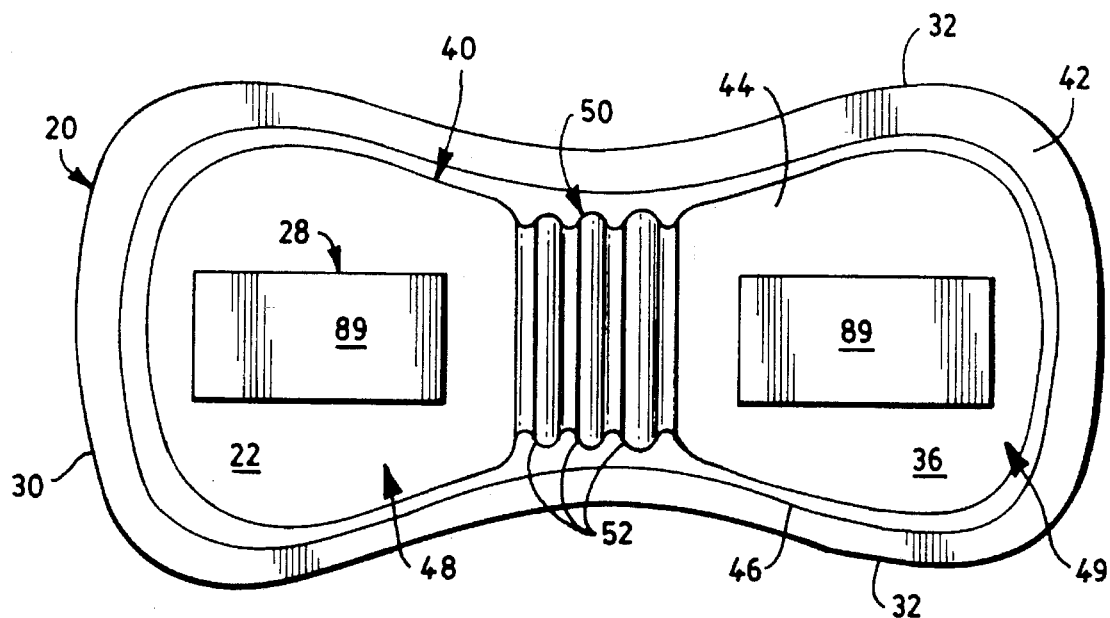
FIG. 3 is a bottom view of the disposable absorbent article shown in FIG. 1.

Within the context of this specification, each term or phrase below will include the following meaning or meanings:

(a) "bonded" refers to the joining, adhering, connecting, attaching, or the like, of two elements. Two elements will be considered to be bonded together when they are bonded directly to one another or indirectly to one another, such as when each is directly bonded to intermediate elements.

(b) "disposable" includes being disposed of after use, and not intended to be washed and reused.

(c) "disposed," "disposed on," "disposed with," "disposed at," "disposed near," and variations thereof are intended to mean that one element can be integral with another element, or that one element can be a separate structure bonded to or connected to or placed with or placed near another element.

(d) "formed" and "formable" describe the condition or property of a material to be conformable to a three-dimensional shape and thereafter generally retain the three-dimensional shape, for example, through the application of heat and pressure to the material in manufacturing processes such as thermoforming, vacuum forming, injection molding, mechanical forming, or the like.

(e) "integral" is used to refer to various portions of a single unitary element rather than separate structures joined to or connected to or placed with or placed near one another.

(f) "liquid communication" means that liquid is able to pass between the specified layers.

(g) "liquid impermeable" when used to describe a layer or laminate means that bodily liquids such as urine will not pass through the layer or laminate under ordinary use conditions in a direction generally perpendicular to the plane of the layer or laminate at the point of liquid contact.

(h) "member" when used in the singular can have the dual meaning of a single element or a plurality of elements.

These terms may be defined with additional language in the remaining portion of the specification.

DETAILED DESCRIPTION OF THE PREFERRED EMBODIMENTS

With reference to FIGS. 1–4, a disposable absorbent article 20 formed according to the present invention is shown for purposes of illustration as a feminine incontinence product. The invention may also be embodied in other types of disposable absorbent articles, such as male incontinence products, feminine hygiene products, wound dressings, or the like. The illustrated absorbent article 20 includes a moisture barrier 22, an absorbent assembly 24 (FIG. 4), a liner 26 and attachment means 28.

The moisture barrier 22 is formed from a flexible, formable material that is substantially liquid impermeable. The moisture barrier 22 has longitudinal end edges 30 and longitudinal side edges 32 extending between the end edges. The side edges 32 are desirably curved so that the moisture barrier 22 is hourglass or I-shaped, although the moisture barrier may also be T-shaped, rectangular, oval, or irregularly-shaped. The moisture barrier 22 has opposite major surfaces designated inner surface 34 and outer surface 36.

As formed, the moisture barrier 22 defines a basin 40 with an integral rim 42 surrounding the basin. The rim 42 forms a generally flat surface that is positioned against the wearer during use. The rim 42 can directly or indirectly contact the wearer, depending on the position of other materials, such as the liner 26. The rim 42 desirably extends continuously around the periphery of the basin 40 and has a generally uniform width.

The basin 40 of the moisture barrier 22 includes a floor 44 and an integral peripheral wall 46 surrounding the floor. The basin 40 has a length dimension, a width dimension, and a height dimension. Accordingly, the basin 40 has a volume into which the absorbent assembly 24 is positioned. The length dimension of the basin 40 is measured parallel to the longitudinal axis of the absorbent article 20 and is generally greater than the width dimension. Conversely, the width dimension is measured perpendicular to the longitudinal axis of the absorbent article 20. The longitudinal axis of the article 20 is depicted by arrow 47 in FIG. 1. The peripheral wall 46 forms an angle with the floor 44, thus giving the basin 40 its height dimension and spacing the rim 42 from the floor. In particular embodiments of the invention, the basin 40 is formed such that the length dimension measures from about 7 to about 30 centimeters, the width dimension measures from about 3 to about 12 centimeters, and the height dimension measures from about 0.2 to about 6 centimeters.

The floor 44 includes first and second longitudinally spaced end regions 48 and 49, which are desirably although not necessarily substantially flat. An extendable region 50 of the floor 44 is located between and separates the first and second end regions 48 and 49. The extendable region 50 of the floor 44 is formed with a plurality of corrugations 52. Each corrugation 52 represents a fold, pleat, set of parallel and alternating ridges and grooves, or the like, in the moisture barrier 22.

Figure 5:
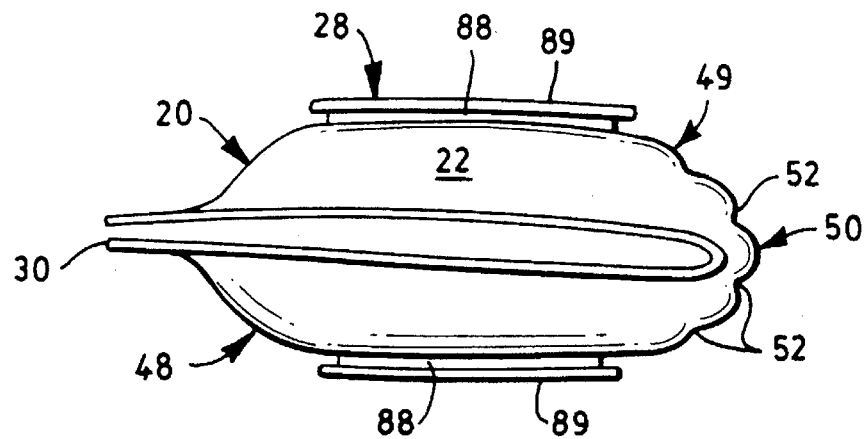
FIG. 5 is a side view of the disposable absorbent article of FIG. 1, but shown in a folded position.

The corrugations 52 permit the absorbent article 20 to bend inwardly, for example to conform to the shape of the wearer, without bunching the moisture barrier 22 along the rim 42. In particular, the extendable region 50 of the floor 44 tends to function as an expandable hinge for the absorbent article 20, extending in length and bending as the absorbent article is bent. As shown in FIG. 5, the corrugations 52 permit the absorbent article 20 to fold inwardly upon itself, such as for packaging. This is accomplished without substantially bunching and folding the moisture barrier 22 along the rim 42, a condition which can generate permanent creases in the rim 42 and lead to side leakage from the article 20. The corrugations 52 also permit the absorbent article 20 to fold inwardly upon itself or against the wearer without substantially stretching or deforming the floor 44 of the moisture barrier 22. In particular, the article 20 can conform to the shape of the wearer without substantially reducing the depth of the basin 40 and its ability to hold the maximum volume of liquid.

The corrugations 52 extend between the side edges 32 of the moisture barrier 22. The longitudinal axis of the fold, pleat, or set of alternating ridges and grooves, or the like, which forms each corrugation 52 is generally parallel to the width dimension of the basin 40, and thus the corrugations 52 are considered to be parallel to the width dimension of the basin. The corrugations 52 desirably do not extend into the rim 42 of the moisture barrier 22. This allows the rim 42 to remain smooth and fit closely to the wearer. Rather, the corrugations 52 desirably extend at least partially into the peripheral wall 46 of the basin 40 on each side of the floor 44. The corrugations 52 may, for example, begin adjacent the rim 42 and gradually increase in depth approaching the floor 44. The maximum depth of the corrugations 52 is desirably maintained across the width of the floor 44.

Depending upon the type of product and its intended use, the manufacturer of the absorbent article 20 may wish to vary the size of each corrugation, the frequency of the corrugations, and the distance over which the corrugations extend, measured along the longitudinal axis 47 of the absorbent article. For example, a relatively few number of relatively large corrugations 52 may be able to provide the same bending characteristics as a relatively large number of relatively small corrugations. Similarly, the frequency or size of the corrugations 52 may be reduced if the corrugations extend over a greater longitudinal length of the absorbent article 20. In general regarding the illustrated absorbent article 20, a greater number of corrugations 52 and/or larger corrugations are required to maintain easy folding capability as the depth of the product is increased.

The size of the corrugations 52 can vary greatly, such as from about one half the thickness of the floor 44 of the formed moisture barrier 22 to about three-quarters of the depth of the basin 40. In the illustrated absorbent article 20, for example, the corrugations may have a depth of from about 0.8 millimeters to about 25 millimeters. Desirably, the corrugations 52 have a depth of from about 2 to about 6 millimeters. One suitable method of determining the depth of a corrugation 52 is to employ a thickness gauge, such as Custom Scientific thickness gauge Model CS-55-325 or equivalent gauge which delivers a 0.1 g/cm$^2$ loading. The portion of the floor 44 containing the corrugations 52 is removed from the article 20 and its thickness measured. A portion of the moisture barrier 22 not containing the corrugations 52, desirably also a portion from the floor 44, is also removed and its thickness measured. The depth of a corrugation is the difference between these two measurements.

For the illustrated absorbent article 20, the frequency of the corrugations 52 may range from 1 to about 96 corrugations every 76 millimeters. Desirably, the frequency of the corrugations 52 ranges from about 2 to about 5 corrugation every 25 millimeters.

The distance over which the corrugations 52 extend along the longitudinal axis of the absorbent article 20 depends in part upon the type of attachment means 28 that are employed. For example, where adhesive is used on the outer surface 36 of the moisture barrier 22 to attach the absorbent article 20 to a garment, the corrugations 52 may extend over a longitudinal distance equating to from about 5 to about 75 percent of the length of the absorbent article. In the illustrated absorbent article 20, the corrugations 52 desirably extend a longitudinal distance of from about 20 to about 35 percent of the length of the absorbent article. In one particular aspect of the invention, the absorbent article 20 is approximately 240 millimeters in length and the corrugations 52 extend over from about 50 to about 75 millimeters of the length. Alternatively, attachment means 28 other than such garment attachment adhesive may be employed, in which case the corrugations 52 may extend over a longitudinal distance up to the full length of the absorbent article (not shown).

Formable materials useful for the moisture barrier 22 include various thermoplastic or thermosetting polymeric resins. The moisture barrier 22 may comprise, for example, polyethylene, polypropylene, polyurethane, polyesters, or the like. In one particular embodiment of the present invention, the moisture barrier 22 is formed from a thin layer of closed-cell, cross-linked polyethylene foam, which may contain a vinyl acetate comonomer, commercially available from Voltek Inc. of Lawrence, Mass., USA, under the trade designation Volara. The foam material prior to forming desirably has a density of about 24 to about 96 kg/m$^3$ and a thickness of about 1.6 to about 9.5 millimeters. Other thermoplastic or thermosetting polymeric foams and materials, such as thermoformable films, nonwovens, or film and nonwoven composites are also suitable for use in the present invention.

Figure 6:
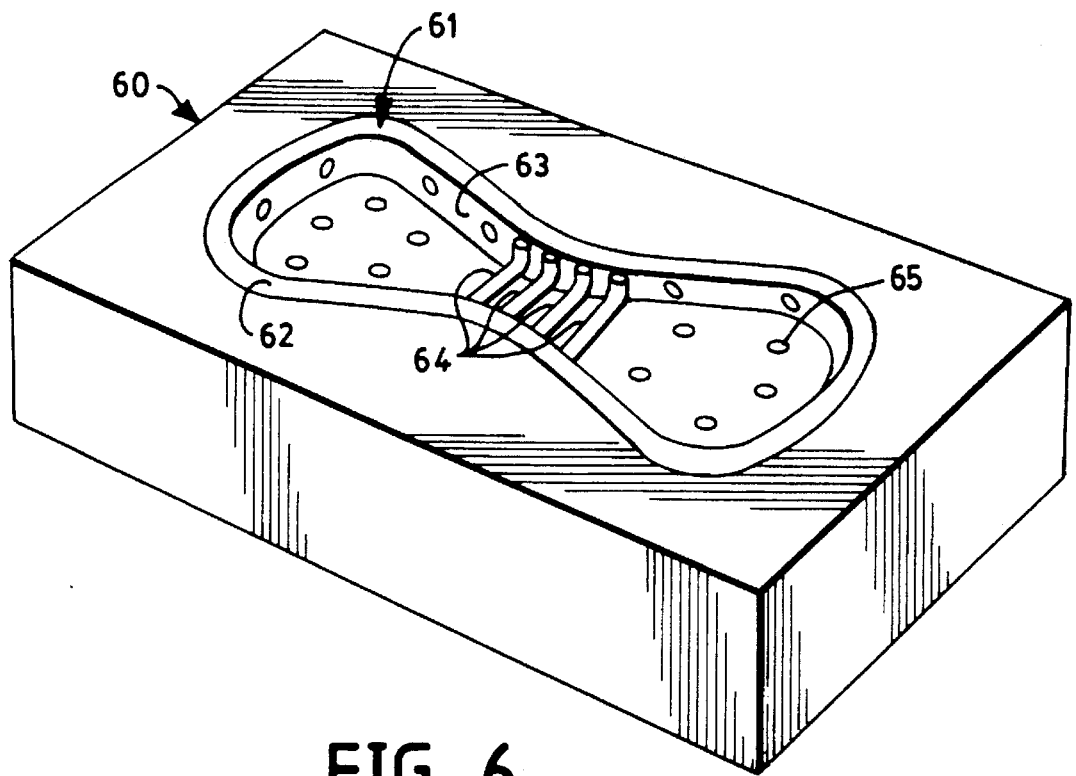
FIG. 6 is a schematic view of a forming mold used to form a moisture barrier of the disposable absorbent article shown in FIG. 1.

The moisture barrier 22 can be formed from a variety of manufacturing processes such as thermoforming, vacuum forming, injection molding, mechanical forming, matched die molding, or the like. In one particular aspect of the invention, the moisture barrier 22 is gas impermeable and formed using a forming mold 60 as shown in FIG. 6. The forming mold 60 includes a mold surface 61 having generally flat peripheral portions 62 for forming the rim 42 of the moisture barrier 22 and a concave central portion 63 for forming the basin 40 of the moisture barrier. The concave central portion 63 includes a plurality of ridges 64 extending transversely across the concave central portion. The ridges 64 are desirably raised portions of the concave central portion which form the corrugations 52 in the moisture barrier 22. A plurality of spaced conduits 65 in the forming mold 60 connect the mold surface 61 with a vacuum source (not shown).

In one aspect of the invention, a sheet of moisture barrier material 22 is heated until the temperature of the moisture barrier material is elevated to its softening point. In one embodiment, the sheet of moisture barrier material 22 is a cross-linked polyethylene foam having a density of about 44 kg/m$^3$ and a thickness of about 2 millimeters, and the material is heated to a temperature of about 115 to 157 degrees Celsius, particularly about 149 degrees Celsius, for a period of about 5 to about 18 seconds, particularly about 8 seconds. Heating temperatures and times will, of course, vary depending upon the particular moisture barrier material 22 selected.

The heated sheet of moisture barrier material 22 is positioned against the forming mold 60 to form a seal therebetween. This seal allows the material to be vacuum drawn onto the mold surface 61. In particular embodiments, the moisture barrier 22 suitably has a formed thickness of from about 1.1 to about 2.0 millimeters, and desirably from about 1.6 to about 1.8 millimeters. After forming, the sheet of moisture barrier material 22 is removed from the forming mold 60, allowed to cool, and cut to the desired dimensions. Alternately, the moisture barrier 22 may be thermoformed using plug assist, a male mold, both male and female molds, drape forming or other suitable techniques (not shown). Other suitable forming techniques are disclosed in commonly assigned U.S. patent application Ser. No. 08/165,153 filed Dec. 9, 1993, by M. K. Melius et al. for a "Formed Incontinence Article And Method Of Manufacture," which is incorporated herein by reference.

One advantage of forming an extendable region 50 in the moisture barrier 22 is that the overall moisture barrier as formed can be generally flat. Previously, formed incontinence products had to be formed in a generally curved shape in the longitudinal direction so that the products would fit closely against the body of the wearer. The present moisture barrier 22, in contrast, can be formed generally flat, and still conform to the body of the wearer due to its bending ability. This provides a manufacturing benefit as well because it is easier to process a moisture barrier 22 that is generally flat than it is to process one that is formed in a longitudinally curved shape, particularly in today's high-speed manufacturing environment.

Figure 7A:
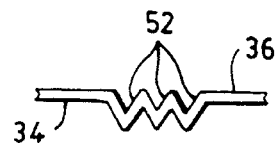
FIGS. 7A through 7E illustrate alternative corrugation patterns which may be formed in the moisture barrier of the disposable absorbent article.
Figure 7B:
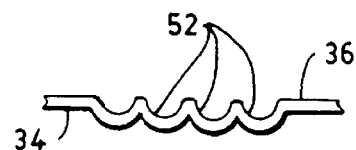
Figure 7C:
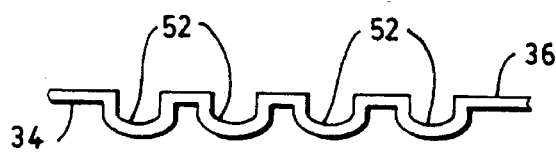
Figure 7D:
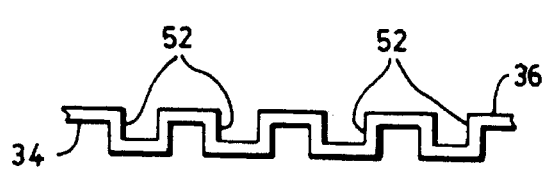
Figure 7E:
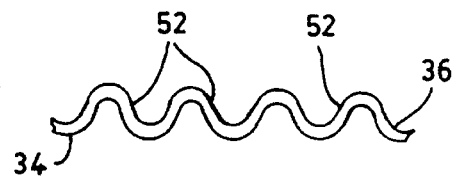

As noted previously, the ridges 64 in the mold surface 61 of the forming mold 60 are desirably raised portions of the concave central portion 63. As a result, the corrugations 52 in the moisture barrier 22 tend to project toward the inner surface 34 and into the basin 40. The ridges 64 may possess a variety of cross-sectional shapes, such as triangular, flared U-shaped, U-shaped, rectangular, or the like. Examples of the corrugations 52 which result from such variously shaped ridges 64 are illustrated in FIGS. 7A through 7D, which show enlarged longitudinal section views through portions of the extendable region 50 of alternative moisture barriers 22. The ridges 64 in the mold surface 61 may alternatively comprise depressed portions of the central portion 63 (not shown). The corrugations 52 resulting from such depressed ridges are illustrated in FIG. 7E. Because these corrugations 52 tend to project toward the outer surface 36 and away from the basin 40, these corrugations would tend to be more noticeable to the wearer. Suitable ridges 64 may include any combination of the forgoing cross-sectional shapes.

Figure 8:
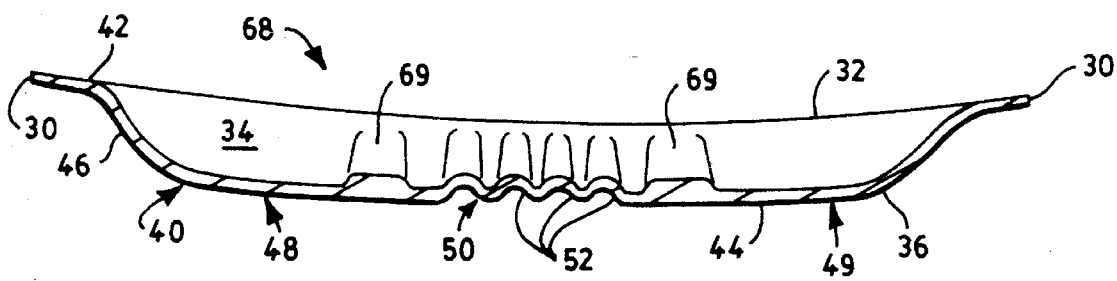
FIG. 8 is a longitudinal section view of an alternative moisture barrier for use in a disposable absorbent article according to the present invention.

Another aspect of the invention is illustrated by an alternative moisture barrier 68 shown in FIG. 8. Components similar to those previously described have been given the same reference numeral. In general, the moisture barrier 68 desirably possesses sufficient structural rigidity to form a stand-alone, three-dimensional shell, while at the same time, providing flexibility at some locations to readily conform to pressures exerted on it during use by a wearer. Not all parts of the moisture barrier 68 are desired to be as flexible, however, and for that reason the moisture barrier 68 of FIG. 8 is formed with rib means 69.

The rib means 69 enhance resistance to transverse compression of the moisture barrier in the extendable regions 50 of the basin 40. The rib means 69 extend parallel to the width dimension of the moisture barrier 22, desirably across the full width of the floor 44 and at least partially up the peripheral wall 46 on each side of the floor. In the illustrated embodiment, the rib means 69 are located on either longitudinal end of the extendable region 50, adjacent the corrugations 52. The rib means 69 could alternatively be located in other regions of the floor, such as between corrugations 52, provided the rib means 69 do not impede bending of the extendable region 50. The moisture barrier 68 may contain a plurality of rib means 69, and desirably comprises from about 2 to about 10 rib means.

The rib means 69 may comprise enhanced thickness portions of the floor 44 as illustrated. Such enhanced thickness portions may be formed integral with the remaining portions of the floor 44 or separately provided and attached to the floor. In one embodiment, the rib means 69 are formed in part by strips, ribbons, rods, fibers, filaments, fabrics, foams, or the like, made from thermoformable or non-thermoformable materials such as polymers, polyethylene, polypropylene, polyesters, or the like. Alternatively, the rib means 69 may comprise heavily densified portions of the floor 44 which have an enhanced resistance to transverse compression of the moisture barrier 68, compared to other portions of the floor. Still alternatively, the rib means 69 may be formed from a single foam sheet that is pleated a plurality of times and thereafter thermoformed.

One suitable method for measuring resistance to transverse compression of the moisture barrier 22 is a Half-Width Compression Test which uses an Instron Model 5213 actuator available from Instron Engineering Corporation, Canton, Mass. The Instron tester includes a 50 kilogram load cell (compression) and is operated with a crosshead speed of 100 millimeters per minute. The procedure uses two half cylinders mounded on the Instron tester so that the curved surfaces of the half cylinders face one another and are movable toward one another. The half cylinders may be formed by longitudinally separating a can having a diameter of 15.24 centimeters into equal halves. After being conditioned in a room which is 21±1 degree Celsius and 50±2 percent relative humidity for a period of two hours, the sample to be tested is positioned on the lower half cylinder such that a peripheral wall 46 that is parallel to the longitudinal axis 47 of the sample is in contact with the curved surface of the half cylinder. The rim 42 of the sample is positioned against an end of the half cylinder so that the basin 40 can rest against the curved surface of the lower half cylinder. The crosshead is lowered until the surface of the upper half cylinder, which is mounted on the crosshead, just touches the basin 40 of the sample. Thus, the longitudinal sides of the basin 40 are positioned between the half cylinders, while the rim 42 is located adjacent the ends of the half cylinders. A plate is positioned against the bodyside surface of the sample and hand held against the sample so that the absorbent assembly 24 of the sample does not bow outward from between the half cylinders as the half cylinders are moved together. The crosshead is actuated so that the distance between the upper and lower half cylinders is reduced by 50 percent, and the peak load registered during that movement is noted.

The absorbent assembly 24 (FIG. 2) is positioned in the basin 40 and disposed on the inner surface 34 of the moisture barrier 22. The absorbent assembly 24 is desirably formed to be sufficiently flexible to readily conform to the contour of the inner surface 34 and be capable of folding inward to the same extent as the moisture barrier 22. The absorbent assembly 24 is desirably moveable relative to the inner surface 34 of the moisture barrier 22 to allow for bending of the absorbent article 20.

Figure 4:
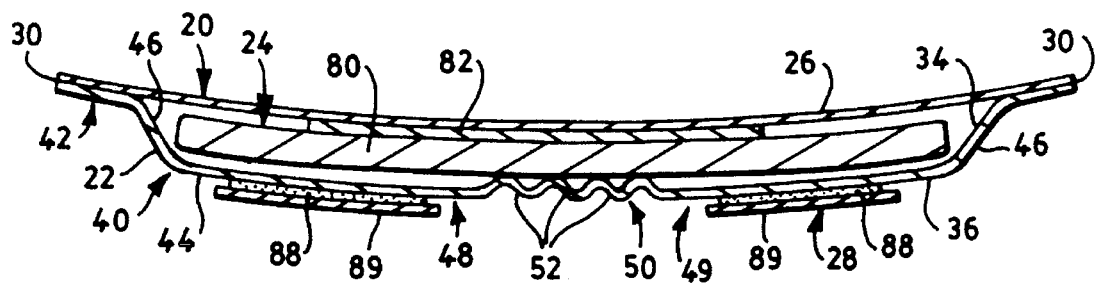
FIG. 4 is a longitudinal section view taken generally from the plane of the line 4–4 in FIG. 1.

The absorbent assembly 24 comprises a liquid storage layer 80 formed of a material adapted to absorb and retain urine, and optionally, an acquisition layer 82 (FIGS. 1 and 4). The absorbent assembly 24 is generally configured according to the amount of liquid intended to be absorbed, and the absorbent rate and capacity of the assembly components. In particular embodiments, the storage layer 80 suitably has a capacity of urine of from about 25 to 400 grams, particularly about 220 grams. The urine capacity of the storage layer 80 is its saturated retention capacity, which is a measure of the total absorbent capacity of an absorbent garment, material or structure after being subjected to 35.1 $g/cm^2$ pressure for five minutes.

The liquid storage layer 80 may comprise various absorbent materials, such as an air-formed batt of cellulosic fibers (i.e., wood pulp fluff) or a coform material composed of a mixture of cellulosic fibers and synthetic polymer fibers. The liquid storage layer 80 may also include compounds to increase its absorbency, such as 0–100 weight percent of organic or inorganic high-absorbency materials, which are typically capable of absorbing at least about 15 and desirably more than 25 times their weight in water. Suitable high-absorbency materials are described in U.S. Pat. Nos. 4,699,823 issued Oct. 13, 1987, to Kellenberger et al. and 5,147,343 issued Sep. 15, 1992, to Kellenberger, which are incorporated herein by reference. High-absorbency materials are available from various commercial vendors, such as Dow Chemical Company, Hoechst Celanese Corporation, and Allied Colloids, Inc.

The storage layer 80 may also include a tissue wrap layer to help maintain the integrity of the fibrous core. This tissue wrap typically comprises a hydrophilic cellulosic material, such as creped wadding or a high wet-strength tissue.

The acquisition layer 82 is superposed on top of and in liquid communication with the storage layer 80. Dots or lines of adhesives, ultrasonic bonds or other suitable means may be employed to bond the acquisition layer 82 to the storage layer 80. The acquisition layer 82 may be generally the same size and shape as the storage layer 80, however it is desired that the acquisition layer be shorter than the storage layer, as illustrated in FIGS. 1 and 4.

The acquisition layer 82 can be or can contain any suitable material for managing, transporting, accommodating, permitting, or directing rapid and/or sudden flow of urine therethrough and into contact with the storage layer 80. The acquisition layer 82 desirably functions to draw liquid from the liner 26 and then permit desorption by the storage layer 80. Included among suitable components for acquisition layer 82 are fibers such as polypropylene, polyethylene, polyester, blends thereof, or the like. One suitable material for the acquisition layer 82 is a latex bonded rayon web, which is available from Sackner Products of Grand Rapids, Mich. under the trade designation SN-92. An acquisition layer 82 of this type desirably has a thickness of about 6.35 millimeters and a basis weight of about 120 grams per square meter. Other suitable materials are disclosed in U.S. Pat. No. 4,798,603 issued Jan. 17, 1989, to Meyer et al., which is incorporated herein by reference.

The liner 26, which is formed of a substantially liquid permeable material, is positioned to sandwich the absorbent assembly 24 between the liner and the moisture barrier 22. Desirably, the liner 26 is directly bonded to the moisture barrier 22 along the rim 42, as shown in FIG. 4. The moisture barrier 22 and liner 26 may be bonded together using adhesives, thermal bonds, ultrasonic bonds or other suitable means. The liner 26 may also be bonded directly to the absorbent assembly 24 using thermal bonds, adhesives, ultrasonic bonds or other suitable means. In an alternate embodiment, the liner 26 is positioned directly over the storage layer 80 and the acquisition layer 82 is bonded to the surface of the liner that is remote from the storage layer (not shown).

The liner 26 may be any soft, flexible, porous sheet which passes fluids therethrough. The liner 26 may comprise, for example, a nonwoven web or sheet of set strength tissue paper, a spunbonded, meltblown or bonded-carded web composed of synthetic polymer filaments, such as polypropylene, polyethylene, polyesters or the like, or a web of natural polymer filaments such as rayon or cotton. The liner 26 has a pore size that readily allows the passage therethrough of liquids, such as urine and other body exudates. The liner 26 may be selectively embossed or perforated with discrete slits or holes extending therethrough, such as an apertured film material. Optionally, the web or sheet may be treated with a surfactant to aid in liquid transfer. One suitable surfactant is identified as Triton X-102 and available from Rohm and Haas Corporation of Philadelphia, Pa., USA. Examples of suitable liner materials include a wettable spunbonded polypropylene web having a basis weight of 24 grams per square meter, and a wettable bonded carded web of polyethylene/polypropylene side-by-side conjugate fibers having a basis weight of 20 grams per square meter.

The attachment means 28 (FIGS. 2–5) of the absorbent article 20 include two strips of garment attachment adhesive 88 secured to the outer surface 36 of the moisture barrier 22. Additionally, removable peel strips 89 cover the attachment adhesive 88 until use and prevent contaminates from contacting the attachment adhesive. In an alternative embodiment, a single peel strip could be used to cover the two spaced strips of attachment adhesive 88 (not shown). Still alternatively, other suitable attachment means such as belts, straps, bodyside adhesives, attachment tapes, mechanical fasteners, or the like, could be used to hold the article in place.

In the illustrated embodiment, the strips of attachment adhesive 88 are disposed on the floor 44 of the basin 40, with one adhesive strip located in each of the first and second end regions 48 and 49. Desirably, the attachment adhesive strips 88 are disposed on the floor 44 solely in these end regions 48 and 49 and not located in the extendable region 50, so that the attachment adhesive 88 does not interfere with extension and retraction of the corrugations 52. In particular embodiments wherein the end regions 48 and 49 also include corrugations (not shown), smaller adhesive strips or other means of attachment can be used.

In use, the wearer removes the peel strips 89 and attaches the attachment adhesive 88 to the inside surface of an undergarment. The attachment adhesive 88 allows the absorbent article 20 to remain in position to receive discharged liquids. While securing the absorbent article 20 and while in use, the article easily bends to fit the undergarment and fit against the body of the wearer. In embodiments employing the lateral rib means 64 (FIG. 8), particular regions of the absorbent article 20 have enhanced resistance to transverse compression.

EXAMPLE

An absorbent article 20 of the type illustrated in FIG. 1 was constructed from the following materials. The moisture barrier 22 was a cross-linked polyethylene foam containing a vinyl acetate comonomer, available from Voltek Inc. of Lawrence, Mass., USA, under the trade designation Volara. The foam material had a density of 64 kg/m$^3$ and a thickness of 1.5 millimeters. The liner 26 was a polyethylene/polypropylene side-by-side conjugate spunbonded material having a basis weight of 20.4 grams per square meter. The storage layer 80 consisted of two separate layers, each a substantially uniform air-laid mixture of wood pulp fluff and high-absorbency. One layer had an hourglass shape and contained wood pulp fluff at 300 grams per square meter and high-absorbency material at 135 grams per square meter. The second layer had a rectangular shape and contained wood pulp fluff at 590 grams per square meter and high-absorbency material at 630 grams per square meter. The two layers were wrapped in tissue and jointly compressed. The acquisition layer was a latex-bonded carded web of rayon fibers material having a basis weight of 120 grams per square meter, available from Sackner Products of Grand Rapids, Mich. under the trade designation SN-92. The garment attachment adhesive was a pressure-sensitive adhesive and the peel strip was a coated paper.

The moisture barrier material 22 was cut into a 38.1 centimeter square sheet. The peripheral 2.54 centimeters of the sheet of moisture barrier material 22 was clamped into a metal frame. The frame and sheet of moisture barrier material were inserted into an oven at a temperature of 270 to 300 degrees Fahrenheit (132°–149° Celsius) for 5 to 7 seconds. The frame and sheet of moisture barrier material were removed from the oven, and the sheet was then drawn by a vacuum into a forming mold like that shown in FIG. 6. The formed moisture barrier material was cooled by a fan for 10 seconds and removed from the metal frame.

Peripheral portions of the moisture barrier material were then cut by hand and removed, leaving the basin 40, the surrounding integral rim 42, and some excess moisture barrier material. The storage layer and acquisition layer were cut to fit in the basin and disposed therein. The liner was heat sealed to the rim 42. The liner and moisture barrier were cut to produce a 1.6 centimeter rim 42 extending around the basin 40. Two strips of garment attachment adhesive 88 were applied to the outer surface 36 of the moisture barrier 22 and covered with peel strips 89.

The foregoing detailed description has been for the purpose of illustration. Thus, a number of modifications and changes may be made without departing from the spirit and scope of the present invention. For instance, alternative or optional features described as part of one embodiment can be used to yield another embodiment. Therefore, the invention should not be limited by the specific embodiments described, but only by the claims.

We claim:

1. An absorbent article, comprising:
   a moisture barrier formed of a formable, liquid impermeable material adapted to retain a three-dimensional shape, the moisture barrier defining a basin with an integral, generally flat rim surrounding the basin, the basin having a width dimension, a length dimension greater than the width dimension, and a volume, the basin comprising a floor having first and second longitudinally spaced end regions and an extendable region between the end regions, the extendable region comprising corrugations formed in the floor parallel to the width dimension, the corrugations adapted to terminate inward of the rim such that the rim remains generally flat, the floor comprising rib means which extend parallel to the width dimension for providing enhanced resistance to transverse compression of the moisture barrier;
   an absorbent assembly disposed within the basin; and
   a liner formed of a liquid permeable material bonded to the moisture barrier and sandwiching the absorbent assembly therebetween.

2. The absorbent article of claim 1, wherein the rib means comprise from about 2 to about 10 enhanced thickness sections which extend over the full width dimension of the floor.

3. The absorbent article of claim 2, wherein the enhanced thickness sections comprise separate members bonded to the moisture barrier.

4. The absorbent article of claim 2, wherein the enhanced thickness sections comprise integral, relatively thicker portions of the floor.

5. The absorbent article of claim 1, wherein the rib means are located at each longitudinal end of the extendable region.

6. The absorbent article of claim 1, wherein the corrugations have a depth of from about 0.8 millimeters to about 25 millimeters.

7. The absorbent article of claim 6, wherein the corrugations have a depth of from about 2 to about 6 millimeters.

8. The absorbent article of claim 6, wherein the maximum depth of the corrugations is maintained across the width of the floor.

9. The absorbent article of claim 1, wherein the corrugations begin adjacent the rim and increase in depth in the direction of the floor.

10. The absorbent article of claim 1, wherein the corrugations occur in a frequency of from 1 to about 96 corrugations every 76 millimeters.

11. The absorbent article of claim 10, wherein the corrugations occur in a frequency of from about 2 to about 5 corrugations every 25 millimeters.

12. The absorbent article of claim 1, wherein the floor has from about 2 to about 100 corrugations.

13. The absorbent article of claim 1, wherein the corrugations extend over a longitudinal distance of from about 5 to about 75 percent of the length of the absorbent article.

14. The absorbent article of claim 1, wherein the corrugations extend over a longitudinal distance of from about 20 to about 35 percent of the length of the absorbent article.

15. An absorbent article adapted for attachment to clothing, the absorbent article comprising:
   a moisture barrier formed of a formable, liquid impermeable material adapted to retain a three-dimensional shape, the moisture barrier defining a basin with an integral, generally flat rim surrounding the basin, the basin having a width dimension, a length dimension greater than the width dimension, and a volume, the basin comprising a floor and a peripheral wall surrounding the floor, the floor having first and second longitudinally spaced end regions and an extendable region between the end regions, the extendable region comprising from about 2 to about 100 corrugations formed in the floor parallel to the width dimension, the corrugations adapted to terminate inward of the rim such that the rim remains generally flat, the floor comprising rib means which extend parallel to the width dimension for providing enhanced resistance to transverse compression of the moisture barrier;
   means for attaching the moisture barrier to clothing, the attaching means comprising an adhesive disposed on the floor solely in the end regions;
   an absorbent assembly disposed within the basin; and
   a liner formed of a liquid permeable material bonded to the moisture barrier and sandwiching the absorbent assembly therebetween.

16. The absorbent article of claim 1, wherein the corrugations in the floor of the moisture barrier project into the basin.

17. The absorbent article of claim 1, wherein the length dimension measures from about 7 to about 30 centimeters, the width dimension measures from about 3 to about 12 centimeters, and the basin has a height dimension measuring from about 0.2 to about 6 centimeters.

\* \* \* \* \*